US012779185B2

(12) United States Patent
Ogido et al.

(10) Patent No.: US 12,779,185 B2
(45) Date of Patent: Nov. 3, 2026

(54) CATHETER INCLUDING CATHETER SHAFT AND DISTAL END TIP

(71) Applicant: ASAHI INTECC CO., LTD., Seto (JP)

(72) Inventors: Moritaka Ogido, Seto (JP); Yutaka Erikawa, Seto (JP); Takeharu Katsurada, Seto (JP)

(73) Assignee: ASAHI INTECC CO., LTD., Seto (JP)

( * ) Notice: Subject to any disclaimer, the term of this patent is extended or adjusted under 35 U.S.C. 154(b) by 453 days.

(21) Appl. No.: 18/380,993

(22) Filed: Oct. 17, 2023

(65) Prior Publication Data

US 2024/0082551 A1 Mar. 14, 2024

Related U.S. Application Data

(63) Continuation of application No. PCT/JP2021/016589, filed on Apr. 26, 2021.

(51) Int. Cl.
*A61M 25/10* (2013.01)
*A61M 25/00* (2006.01)

(52) U.S. Cl.
CPC .... *A61M 25/1034* (2013.01); *A61M 25/0052* (2013.01); *A61M 25/008* (2013.01); *A61M 2025/0081* (2013.01); *A61M 2025/1084* (2013.01); *A61M 2025/1093* (2013.01); *A61M 2205/02* (2013.01)

(58) Field of Classification Search
CPC ............ A61M 25/008; A61M 25/1034; A61M 25/0052; A61M 25/0068; A61M 25/0069; A61M 2025/0081
See application file for complete search history.

(56) References Cited

U.S. PATENT DOCUMENTS

| | | | | |
|---|---|---|---|---|
| 4,490,138 | A * | 12/1984 | Lipsky | A61M 1/84 604/40 |
| 5,092,848 | A | 3/1992 | deCiutiis | |
| 5,762,637 | A | 6/1998 | Berg et al. | |
| 6,918,920 | B1 | 7/2005 | Wang et al. | |
| 9,757,536 | B2 * | 9/2017 | Abt | B29C 66/02241 |
| 2012/0271232 | A1 * | 10/2012 | Katsurada | A61M 25/008 604/524 |
| 2015/0231375 | A1 | 8/2015 | Kubo et al. | |
| 2017/0113018 | A1 | 4/2017 | Shimizu et al. | |
| 2018/0056032 | A1 * | 3/2018 | Shimizu | A61M 25/005 |
| 2018/0078743 | A1 | 3/2018 | Kubo et al. | |
| 2019/0184135 | A1 | 6/2019 | Shimizu | |
| 2020/0353217 | A1 | 11/2020 | Kawashima et al. | |

FOREIGN PATENT DOCUMENTS

| | | | | |
|---|---|---|---|---|
| EP | 0 537 895 | A1 | 4/1993 | |
| EP | 4591915 | A1 * | 7/2025 | A61M 25/10 |
| JP | H05-192410 | A | 8/1993 | |
| JP | H08-187292 | A | 7/1996 | |
| JP | 2015-156880 | A | 9/2015 | |
| JP | 2017-079976 | A | 5/2017 | |
| WO | 2018/055706 | A1 | 3/2018 | |
| WO | 2018/181962 | A1 | 10/2018 | |
| WO | 2019/150427 | A1 | 8/2019 | |

* cited by examiner

*Primary Examiner* — Rebecca E Eisenberg
(74) *Attorney, Agent, or Firm* — Oliff PLC

(57) ABSTRACT

A catheter includes a hollow catheter shaft, and a distal tip connected to a distal end portion of the catheter shaft. A recess is formed in the distal end portion of the catheter shaft, and a proximal end portion of the distal tip is inserted into the recess. According to this catheter, joint strength of the distal tip and the catheter shaft can be enhanced.

14 Claims, 13 Drawing Sheets

CATHETER INCLUDING CATHETER SHAFT AND DISTAL END TIP

CROSS-REFERENCE TO RELATED APPLICATIONS

This application is a continuation of International Application No. PCT/JP2021/016589, filed Apr. 26, 2021. The disclosure of the prior application is hereby incorporated by reference herein in its entirety.

TECHNICAL FIELD

The technology disclosed herein relates to a catheter.

BACKGROUND

A catheter is a long medical device inserted to a body cavity such as a blood vessel for assisting a guide wire inserted to a lesion (constricted part or occluded part) or treating a lesion in a body cavity. A catheter includes a cylindrical catheter shaft, and a cylindrical distal tip fixed to a distal end of the catheter shaft. Hollow portions of the catheter shaft and the distal tip function as lumens to which a guide wire is inserted, for example.

At the time of inserting a catheter into a lesion, a distal tip may be caught (stuck) by the lesion. When a professional pulls the catheter to a proximal end side in the state where the distal tip is caught by the lesion, a tension load is applied to the distal tip in an axial direction of the catheter, so that a joint part of the distal tip and a catheter shaft may be broken and the distal tip may be detached from an inner shaft.

There is known a technology of providing, in a catheter, a tube integrally covering the proximal end portion of the distal tip and the distal end portion of the catheter shaft from the outer periphery in order to prevent breakage of the joint part of the distal tip and the catheter shaft (for example, see Patent Literature 1).

CITATION LIST

Patent Literature

Patent Literature 1: U.S. Pat. No. 6,918,920

SUMMARY

Technical Problem

The technology described above does not directly improve the strength of the joint part of the distal tip and the catheter shaft but indirectly reinforces the joint part by using the tube provided in the outer periphery of the joint part, and the technology described above cannot sufficiently enhance the joint strength of the distal tip and the catheter shaft. Such a problem is not limited to a balloon catheter and is a common problem for catheters including a hollow catheter shaft and a cylindrical distal tip fixed to a distal end of the catheter shaft.

Technology capable of solving the above problems is disclosed herein.

Solution to Problem (1) A catheter disclosed herein includes a catheter shaft including a distal end portion and a proximal end portion, and a distal tip connected to the distal end portion of the catheter shaft. The distal end portion of the catheter shaft is formed with a recess at the distal end of the catheter shaft or a position close to the proximal end side from the distal end. The distal tip includes a proximal end portion that enters the recess.

In this catheter, since the proximal end portion of the distal tip enters the recess formed in the catheter shaft, a contact area of the distal tip and the catheter shaft increases and the proximal end portion of the distal tip functions as an anchor. Therefore, according to this catheter, the joint strength of the distal tip and the catheter shaft can be sufficiently enhanced, and detachment of the distal tip from the catheter shaft can be effectively prevented.

(2) The catheter described above may have a configuration including a reinforcing body embedded in the catheter shaft and formed of a coil or braiding. According to this catheter, since the catheter shaft is reinforced by the reinforcing body, the catheter can be provided with safety maintained.

(3) The catheter described above may have a configuration in which the distal end of the reinforcing body is arranged at a position spaced from the recess to the proximal end side of the catheter shaft. According to this catheter, since the reinforcing body is prevented from being exposed from the catheter shaft even when heat or a mechanical force is applied, for example, at the time of forming the recess in the catheter shaft or at the time of fixing the distal tip to the catheter shaft, the catheter can be provided with safety maintained more.

(4) The catheter described above may have a configuration in which at least a portion of the proximal end portion of the distal tip extends in a direction substantially orthogonal to a center axis of the catheter from an outer peripheral side of the catheter to the center axis side, or in a diagonal direction from the proximal end side to the distal end side, in a longitudinal sectional view of the catheter. According to this catheter, since the proximal end portion of the distal tip further enters the inside of the catheter shaft, the proximal end portion can function as a more effective anchor. Therefore, the joint strength of the distal tip and the catheter shaft can be more effectively enhanced, and detachment of the distal tip from the catheter shaft can be more effectively prevented.

(5) The catheter described above may include a configuration in which the distal tip is made of a resin material having lower hardness than hardness of a resin material forming the catheter shaft. According to this catheter, since the distal tip is made of the resin material having comparatively low hardness, flexibility of the distal end of the catheter can be secured, and a tissue in the body can be prevented from being damaged by the distal end of the catheter. According to this catheter, since the catheter shaft is made of the resin material having comparatively high hardness, even when the heated material of the distal tip is input into the recess after the recess is formed in the catheter shaft, the shape of the distal end portion of the catheter shaft is maintained, and thereby, it is possible to easily and reliably achieve the configuration in which the proximal end portion of the distal tip enters the recess.

(6) The catheter described above may further include a balloon including a distal end side fixation portion, and may have a configuration in which the distal end side fixation portion of the balloon is connected to at least one of the distal tip and the catheter shaft.

In this catheter, since the proximal end portion of the distal tip enters the recess formed in the catheter shaft, a contact area of the catheter shaft and the distal tip increases and the proximal end portion of the distal tip functions as an anchor. Therefore, according to this catheter, the joint strength of the distal tip and the catheter shaft can be sufficiently enhanced, and detachment of the distal tip from the catheter shaft can be effectively prevented. In this catheter, the distal end side fixation portion of the balloon can be prevented from being peeled due to a malfunction of the joint part of the distal tip and the catheter shaft.

Note that the technology disclosed herein can be achieved in various aspects, such as catheters, balloon catheters, and methods for producing the same.

DETAILED DESCRIPTION

A. First Embodiment

A-1. Configuration of Catheter 110

Figure 1:
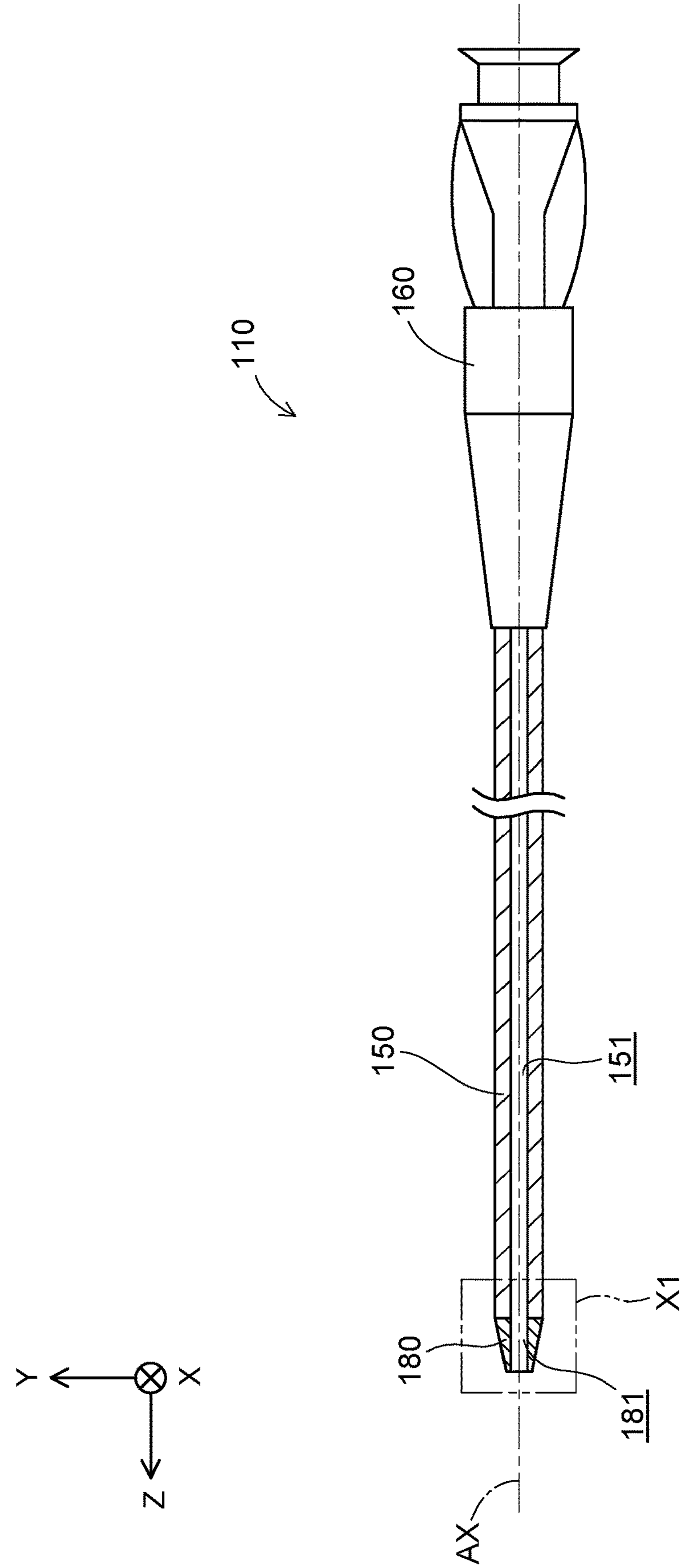
FIG. 1 is a diagram that schematically shows the configuration of a catheter in a first embodiment.

FIG. 1 is a diagram that schematically shows the configuration of a catheter 110 in a first embodiment. FIG. 1 shows a configuration of a longitudinal section including a center axis AX of the catheter 110. For convenience of illustration, regarding some configurations of the catheter 110, a cross sectional configuration is not shown but a side surface configuration is shown, and some configurations of the catheter 110 are not shown. In FIG. 1, Z axis positive direction side is the distal end side (distal side) to be inserted to a body, and Z axis negative direction side is the proximal end side (proximal side, near side) to be operated by a professional such as a doctor. FIG. 1 shows a state where the catheter 110 is a straight line approximately parallel to the Z axis direction, as a whole, but the catheter 110 is flexible enough to be bent. Note that herein regarding the catheter 110 and each configuration member thereof, an end on the distal end side is referred to as "distal end", the distal end and a portion in the vicinity thereof are referred to as "distal end portion", an end on the proximal end side is referred to as "proximal end", and the proximal end and a portion in the vicinity thereof are referred to as "proximal end portion".

The catheter 110 is a long medical device used by being inserted to a body cavity such as a blood vessel, alimentary canal, or ureter or a tissue in a body of a human. The full length of the catheter 110 is about 1500 mm, for example. The catheter 110 includes a catheter shaft 150, a distal tip 180, and a connector 160 connected to the proximal end of the catheter shaft 150.

The catheter shaft 150 is a hollow long member formed with a lumen 151 to which a guide wire (not shown) is inserted, for example. The outer diameter of the catheter shaft 150 ranges from about 0.2 mm to 2.0 mm, for example.

The catheter shaft 150 is made of a resin material. It is preferable that a resin material having a flexible property and appropriate flexibility be used as the resin material for forming the catheter shaft 150. Examples of such a resin material include a polytetrafluoroethylene (PTFE) and a polyamide elastomer.

The distal tip 180 is a hollow member connected to the distal end portion of the catheter shaft 150. The distal tip 180 is formed with a lumen 181 forming an integrated lumen by communicating with the lumen 151 of the catheter shaft 150. In the present embodiment, the distal tip 180 includes a tapered outer peripheral surface having a diameter gradually decreasing from the proximal end side to the distal end side.

The distal tip 180 is made of a resin material. As the resin material for forming the distal tip 180, a resin material having higher flexibility (in other words, having lower hardness) than that of the resin material forming the catheter shaft 150 is used. As the resin material for forming the distal tip 180, a resin material having lower melt viscosity than that of the resin material forming the catheter shaft 150 is used. Examples of such a resin material include a polyurethane elastomer in a case where the catheter shaft 150 is made of polytetrafluoroethylene or a polyamide elastomer.

Figure 2:
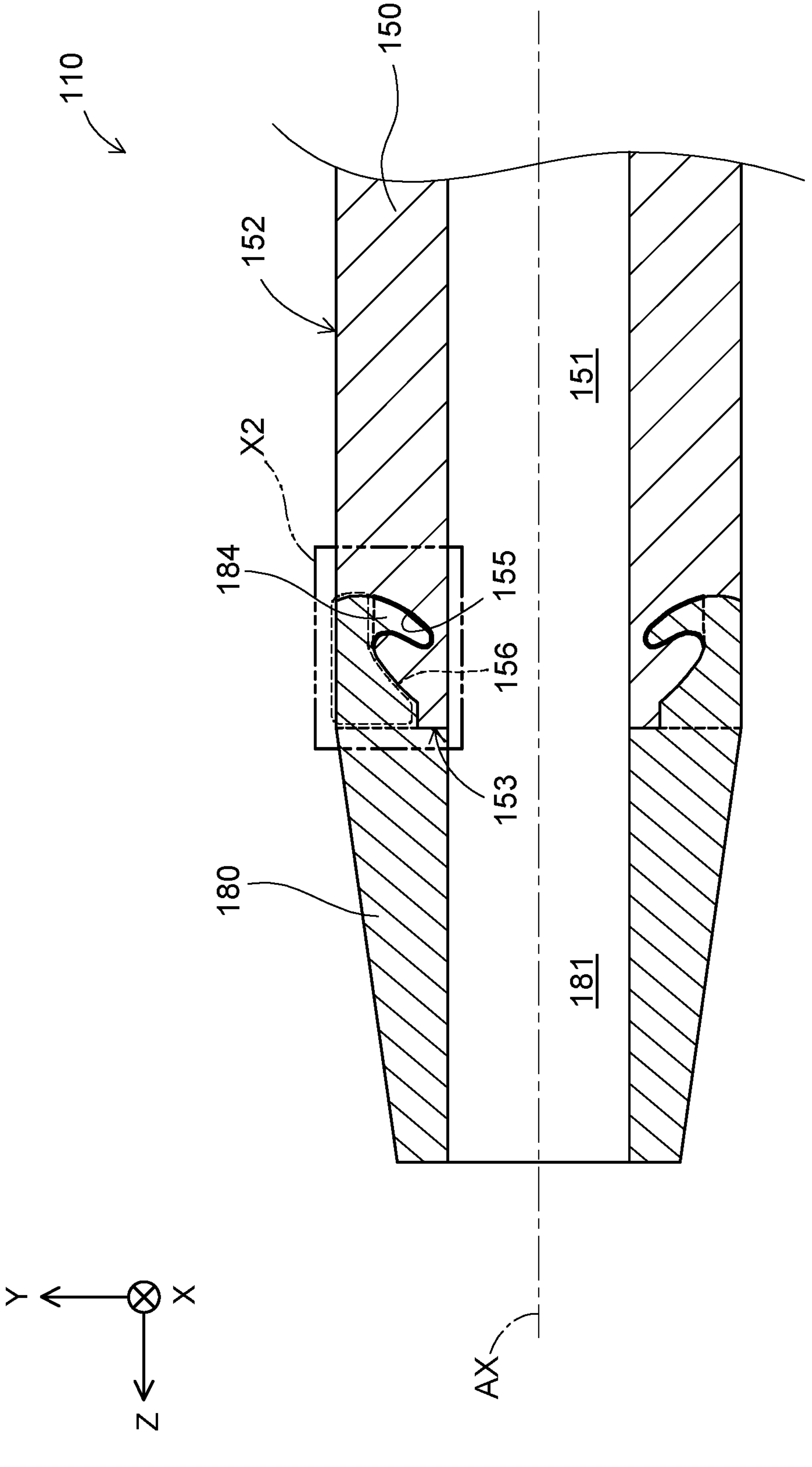
FIG. 2 is a diagram that shows a detailed configuration of a vicinity of a joint part of a catheter shaft and a distal tip in the catheter of the first embodiment.
Figure 3:
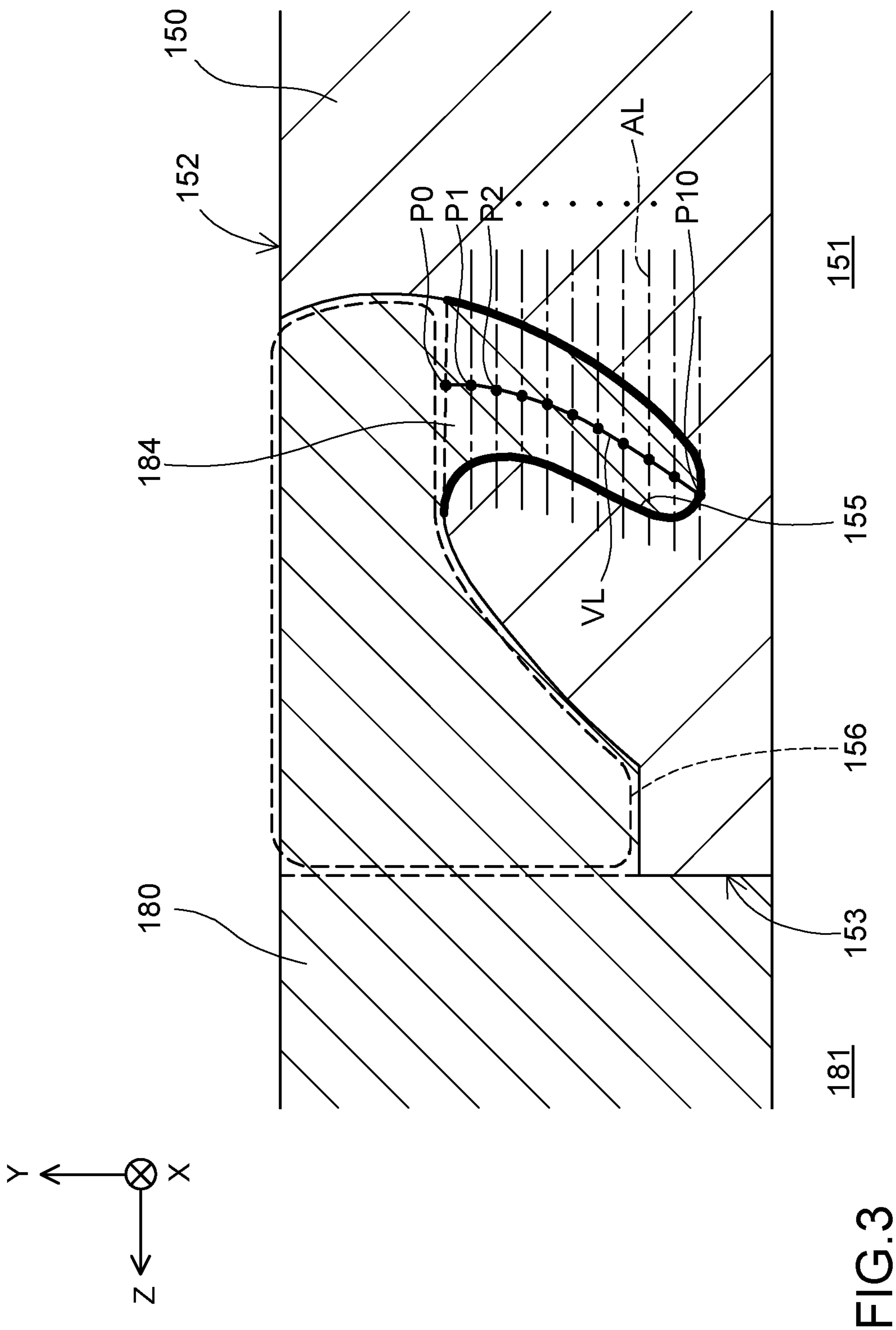
FIG. 3 is a diagram that shows a detailed configuration of a vicinity of the joint part of the catheter shaft and the distal tip in the catheter of the first embodiment.

FIGS. 2 and 3 are diagrams that show a detailed configuration of a vicinity of the joint part of the catheter shaft 150 and the distal tip 180 in the catheter 110 of the first embodiment. FIG. 2 shows the configuration of a longitudinal section (YZ section) of X1 portion of FIG. 1 in an enlarged manner, and FIG. 3 shows the configuration of a longitudinal section (YZ section) of X2 portion of FIG. 2.

As shown in FIGS. 2 and 3, the distal end portion of the catheter shaft 150 is formed with a recess 155. Herein the recess 155 of the catheter shaft 150 means a recess extending from the outer peripheral side of the catheter 110 to the side close to the center axis AX, the recess being surrounded by the catheter shaft 150 in a direction parallel to the center axis AX. Therefore, the recess 155 of the catheter shaft 150 is a portion indicated by a thick line in FIG. 3, and the portions (hereinafter, referred to as a "deficit portion 156") indicated by being surrounded by dashed lines in FIGS. 2 and 3 do not correspond to the recess. As shown in FIGS. 2 and 3, the recess 155 is located at the proximal end side from the distal end 153 of the catheter shaft 150. In the present embodiment, the recess 155 opens in the outer peripheral surface of the catheter shaft 150.

The proximal end portion 184 of the distal tip 180 enters the recess 155 of the catheter shaft 150. In the present embodiment, the proximal end portion 184 of the distal tip 180 is filled in the recess 155 with almost no gap.

In the present embodiment, in at least one longitudinal section (for example, the longitudinal section shown in FIG. 3) including the center axis AX of the catheter 110, the proximal end portion 184 of the distal tip 180 (the portion of the distal tip 180 that enters the recess 155) extends in a diagonal direction from the proximal end side to the distal end side from the outer peripheral side of the catheter 110 to the center axis AX side (in the example of FIG. 3, from upward to downward). Here, the method of specifying the extension direction of the proximal end portion 184 of the distal tip 180 in the section described above is as follows. First, in the section described above, auxiliary lines AL (including a line passing an upper end of the proximal end portion 184 and a line passing a lower end of the proximal end portion 184) that equally divide the height of the proximal end portion 184 into ten are drawn at intervals along a direction extending from the outer peripheral side to the center axis AX side of the catheter 110 (in the example of FIG. 3, a direction extending from upward to downward, and hereinafter, also referred to as a "height direction). Next, division points P0, P1, . . . , P10 for equally dividing the width of the proximal end portion 184 in the center axis AX direction into two are specified using the positions of the auxiliary lines AL. Then, virtual lines VL connecting adjacent division points in straight are sequentially drawn for each of the division points P0 to P10. The direction of the virtual lines is regarded as the extension direction of the proximal end portion 184. As shown in FIG. 3, in the present embodiment, the extension direction of the proximal end portion 184 is a diagonal direction extending from the proximal end side to the distal end side over the entire height direction.

In the present embodiment, the configuration of the joint part of the distal tip 180 and the catheter shaft 150 is similar over the entire circumference of the catheter 110. That is, the catheter 110 of the present embodiment has the configuration shown in FIGS. 2 and 3 of the joint part of the distal tip 180 and the catheter shaft 150 in any cross section including the center axis AX of the catheter 110.

The above-mentioned joint configuration of the catheter shaft 150 and the distal tip 180 can be manufactured by the method described below, for example. Specifically, after the catheter shaft 150 is manufactured, for example, by applying laser processing to the distal end portion of the catheter shaft 150, the recess 155 and a deficit portion 156 are formed. At this time, by adjusting laser output or irradiation direction, shapes of the recess 155 and the deficit portion 156 are adjusted. Thereafter, inputting the formation material of the distal tip 180 that has been softened by heating to the recess 155 and the deficit portion 156 to perform molding. As a result, the distal tip 180 having a configuration in which the proximal end portion 184 enters the recess 155 is manufactured.

The formation of the recess 155 and the deficit portion 156 of the catheter shaft 150 can be achieved by another method. Examples of such another method include a method of embedding a coil in the inside of the catheter shaft 150 and then removing a coil body at a position where the recess 155 and the deficit portion 156 are to be provided. The recess 155 and the deficit portion 156 may not be formed in the catheter shaft 150 in advance, and such a configuration may be adopted that the recess 155 is formed when the proximal end portion 184 of the distal tip 180 enters the distal end portion of the catheter shaft 150 as a result of jointing of the distal tip 180 to the catheter shaft 150.

A-2. Effect of First Embodiment:

As described above, the catheter 110 of the present embodiment includes the catheter shaft 150 and the distal tip 180. The catheter shaft 150 is a member including a distal end portion and a proximal end portion. The distal tip 180 is connected to the distal end portion of the catheter shaft 150. The distal end portion of the catheter shaft 150 is formed with the recess 155 at a position close to the proximal end side from the distal end 153 of the catheter shaft 150. The distal tip 180 includes the proximal end portion 184 that enters the recess 155.

As described above, in the catheter 110 of the present embodiment, since the proximal end portion 184 of the distal tip 180 enters the recess 155 formed in the catheter shaft 150, a contact area of the distal tip 180 and the catheter shaft 150 increases and the proximal end portion 184 of the distal tip 180 functions as an anchor. Therefore, according to the catheter 110 of the present embodiment, the joint strength of the distal tip 180 and the catheter shaft 150 can be sufficiently enhanced, and detachment of the distal tip 180 from the catheter shaft 150 can be effectively prevented even when a tension load to the axial direction of the catheter 110 is applied.

In the catheter 110 of the present embodiment, at least a portion of the proximal end portion 184 of the distal tip 180 extends in a diagonal direction from the proximal end side to the distal end side from an outer peripheral side of the catheter 110 to the center axis AX side of the catheter 110, in a longitudinal sectional view of the catheter 110. Therefore, according to the catheter 110 of the present embodiment, since the proximal end portion 184 of the distal tip 180 further enters the inside of the catheter shaft 150, the proximal end portion 184 can function as a more effective anchor. Therefore, according to the catheter 110 of the present embodiment, the joint strength of the distal tip 180 and the catheter shaft 150 can be highly effectively enhanced, and detachment of the distal tip 180 from the catheter shaft 150 can be highly effectively prevented.

In the catheter 110 of the present embodiment, the catheter shaft 150 is made of a resin material, and the distal tip 180 is made of a resin material having lower hardness than hardness of the resin material for forming the catheter shaft 150. According to the catheter 110 of the present embodiment, since the distal tip 180 is made of the resin material having comparatively low hardness, flexibility of the distal end of the catheter 110 can be secured, and a tissue in the body can be prevented from being damaged by the distal end of the catheter 110. According to the catheter 110 of the present embodiment, since the catheter shaft 150 is made of the resin material having comparatively high hardness, even when the heated material of the distal tip 180 is input into the recess 155 after the recess 155 is formed in the catheter shaft 150, the shape of the distal end portion of the catheter shaft 150 is maintained, and thereby, it is possible to easily and reliably achieve the configuration in which the proximal end portion 184 of the distal tip 180 enters the recess 155.

A-3. Modification Example of First Embodiment:

FIGS. 4A to 6 are diagrams that show each modification example of the first embodiment. In the modification example shown in FIG. 4A, the extension direction of the proximal end portion 184 of the distal tip 180 is different from that in the above-mentioned first embodiment. That is, in the modification shown in FIG. 4A, the proximal end portion 184 of the distal tip 180 extends in a direction (in the example of FIG. 4A, a direction parallel to the Y axis) substantially orthogonal to the center axis AX from the outer peripheral side of the catheter 110 to the center axis AX side. Also in the configuration of the modification example shown in FIG. 4A, since the proximal end portion 184 of the distal tip 180 enters the recess 155 formed in the catheter shaft 150, the contact area of the distal tip 180 and the catheter shaft 150 increases, and the proximal end portion 184 functions as an anchor. Therefore, the joint strength of the distal tip 180 and the catheter shaft 150 can be sufficiently enhanced and the distal tip 180 can be effectively prevented from being detached from the catheter shaft 150.

Figure 4A:
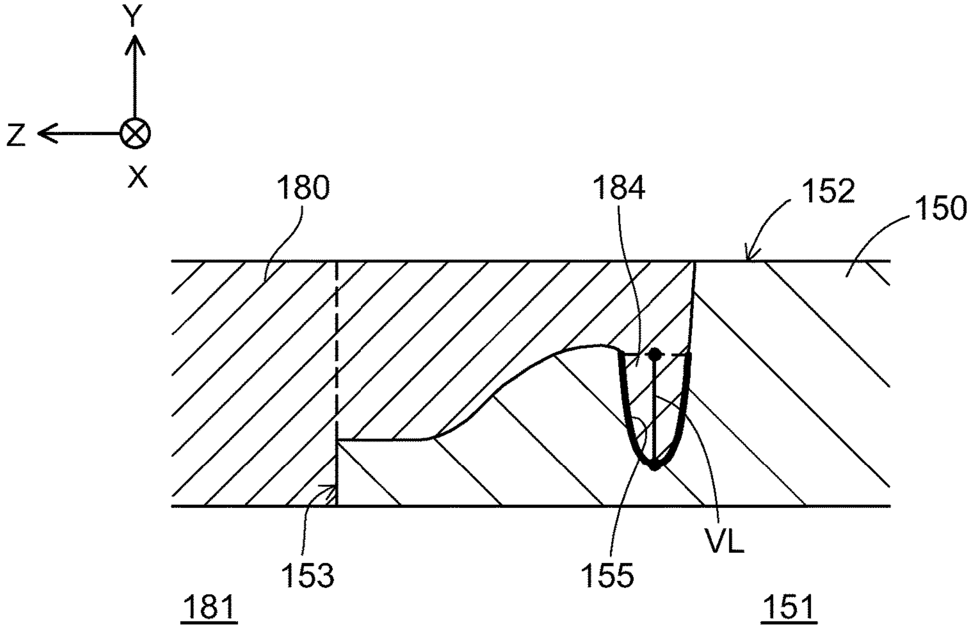
FIGS. 4A and 4B are diagrams that show modification examples of the first embodiment.
Figure 4B:
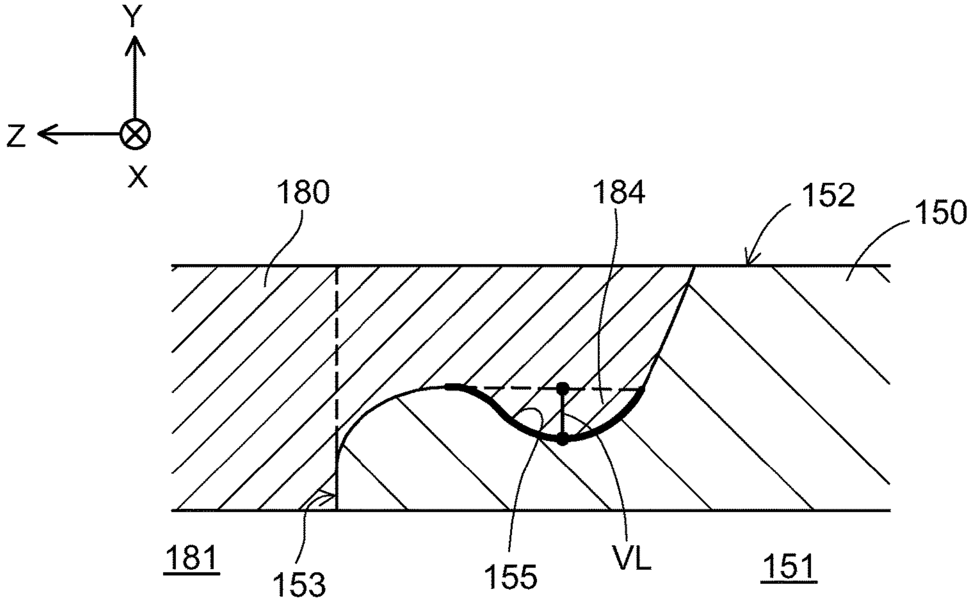

The modification example shown in FIG. 4B is different from the modification example shown in FIG. 4A in that the height of the proximal end portion 184 of the distal tip 180 is relatively low (the depth of the recess 155 is relatively shallow). Also in the configuration of the modification example shown in FIG. 4B, since the proximal end portion 184 of the distal tip 180 enters the recess 155 formed in the catheter shaft 150, the contact area of the distal tip 180 and the catheter shaft 150 increases, and the proximal end portion 184 functions as an anchor. Therefore, the joint strength of the distal tip 180 and the catheter shaft 150 can be sufficiently enhanced and the distal tip 180 can be effectively prevented from being detached from the catheter shaft 150.

Figure 5A:
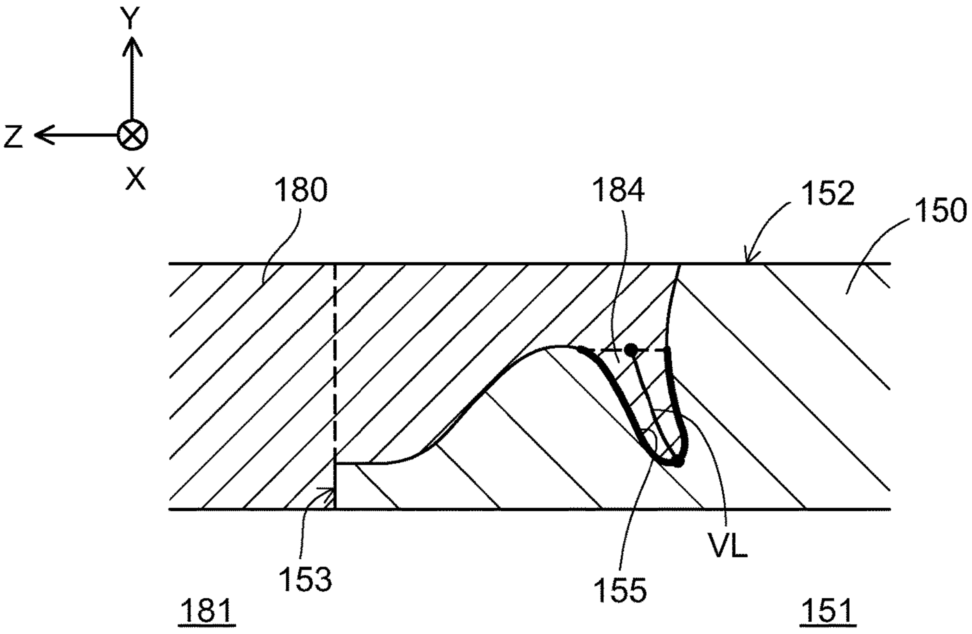
FIGS. 5A and 5B are diagrams that show modification examples of the first embodiment.

In the modification example shown in FIG. 5A, the extension direction of the proximal end portion 184 of the distal tip 180 is different from that in the above-mentioned first embodiment. That is, in the modification shown in FIG. 5A, the proximal end portion 184 of the distal tip 180 extends in a direction (in the example of FIG. 5A, a diagonal direction extending from upper left to lower right) extending from the distal end side to the proximal end side to the center axis AX from the outer peripheral side of the catheter 110 to the center axis AX side. Also in the configuration of the modification example shown in FIG. 5A, since the proximal end portion 184 of the distal tip 180 enters the recess 155 formed in the catheter shaft 150, the contact area of the distal tip 180 and the catheter shaft 150 increases, and the proximal end portion 184 functions as an anchor. Therefore, the joint strength of the distal tip 180 and the catheter shaft 150 can be sufficiently enhanced and the distal tip 180 can be effectively prevented from being detached from the catheter shaft 150.

Figure 5B:
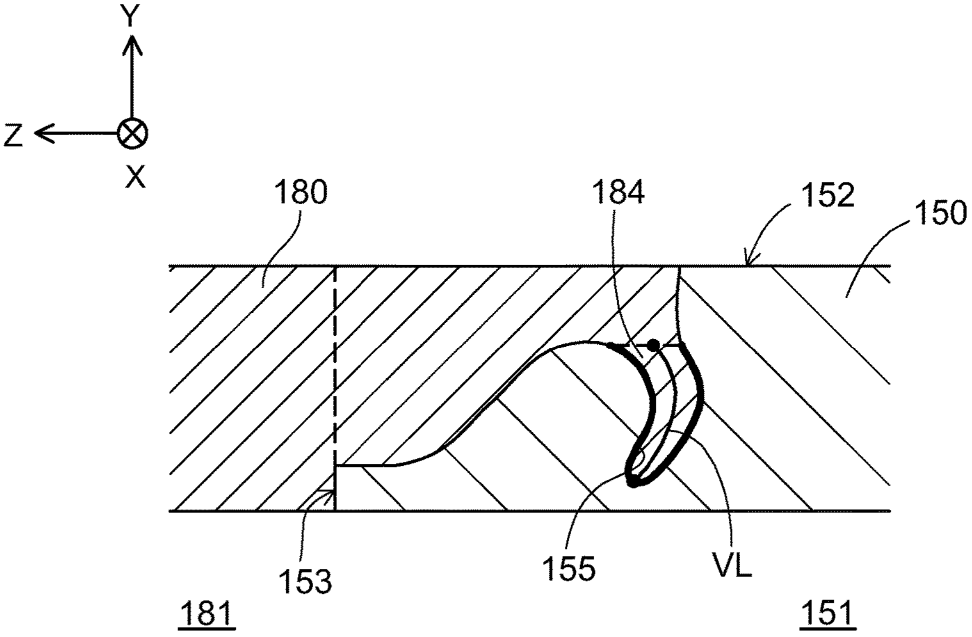

In the modification example shown in FIG. 5B, the extension direction of the proximal end portion 184 of the distal tip 180 is different from that in the above-mentioned first embodiment. That is, in the modification example shown in FIG. 5B, a portion of the proximal end portion 184 of the distal tip 180 in a side (upper side) close to the outer periphery of the catheter 110 extends in a diagonal direction (in the example of FIG. 5B, a direction extending from upper left to lower right) from the distal end side to the proximal end side, from the outer peripheral side to the center axis AX side of the catheter 110, and on the other hand, a portion of the proximal end portion 184 in a side (lower side) close to the center axis AX extends in a diagonal direction (in the example of FIG. 5B, a direction extending from upper right to lower left) extending from the proximal end side to the distal end side, from the outer peripheral side to the center axis AX side of the catheter 110. Also in the configuration of the modification example shown in FIG. 5B, since the proximal end portion 184 of the distal tip 180 enters the recess 155 formed in the catheter shaft 150, the contact area of the distal tip 180 and the catheter shaft 150 increases, and the proximal end portion 184 functions as an anchor. Therefore, the joint strength of the distal tip 180 and the catheter shaft 150 can be sufficiently enhanced and the distal tip 180 can be effectively prevented from being detached from the catheter shaft 150.

Figure 6:
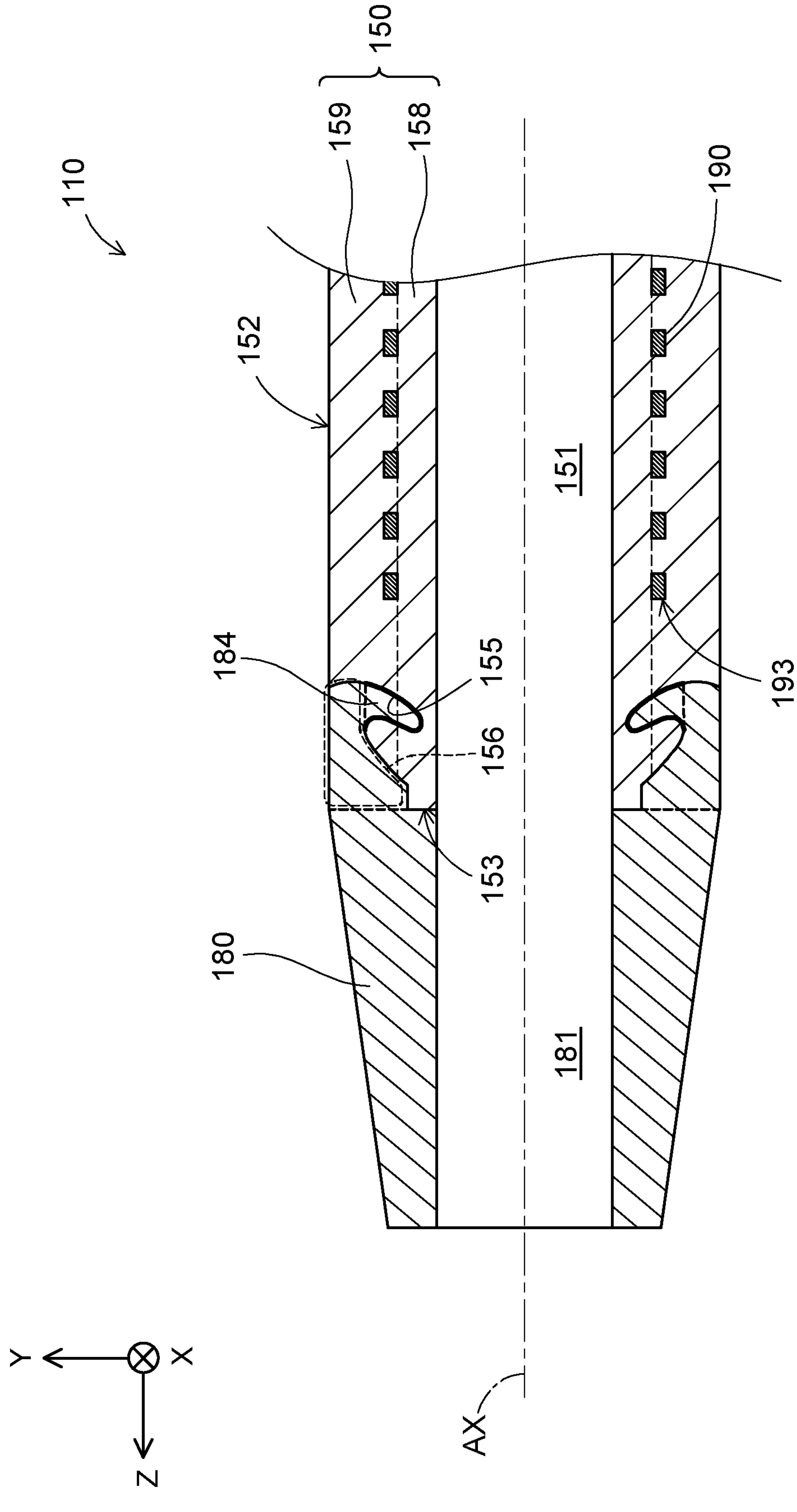
FIG. 6 is a diagram that shows a modification example of the first embodiment.

In the modification example shown in FIG. 6, the catheter shaft 150 is a two-layer tube including a hollow inner layer 158 and an outer layer 159 covering the outer periphery of the inner layer 158. A coil made of metal, for example, is arranged as a reinforcing body 190 in between the inner layer 158 and the outer layer 159. The distal end 193 of the reinforcing body 190 is arranged at a position spaced from the recess 155 of the catheter shaft 150 to the proximal end side. According to the modification example shown in FIG. 6, since the catheter shaft 150 is reinforced by the reinforcing body 190, the catheter 110 can be provided with safety maintained. According to the modification example shown in FIG. 6, since the reinforcing body 190 is prevented from being exposed from the catheter shaft 150 even when heat or a mechanical force is applied, for example, at the time of forming the recess 155 in the catheter shaft 150 or at the time of fixing the distal tip 180 to the catheter shaft 150, the catheter 110 can be provided with safety maintained more.

B. Second Embodiment

B-1. Configuration of Balloon Catheter 10

Figure 7:
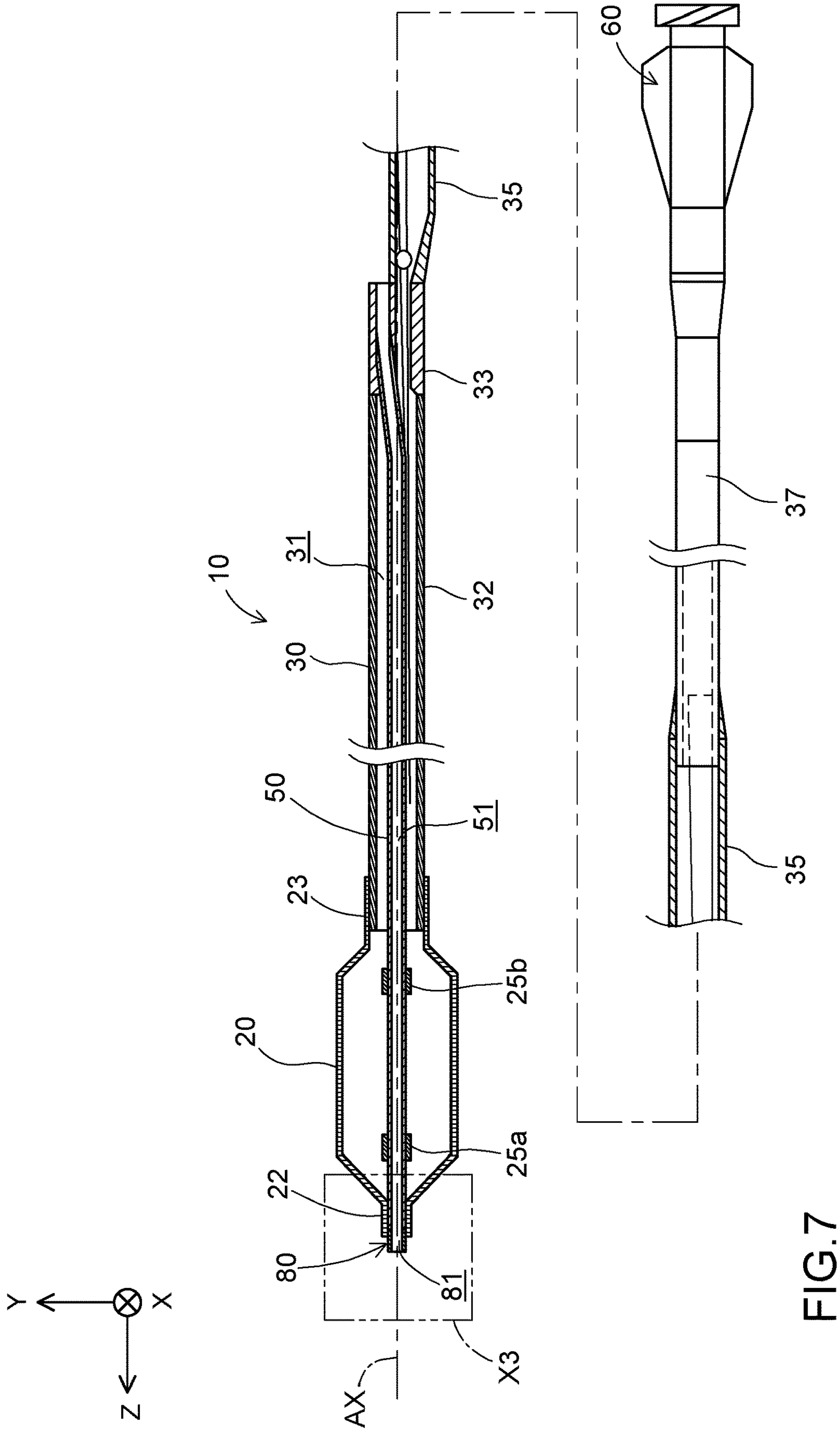
FIG. 7 is a diagram that schematically shows the configuration of a balloon catheter 10 in a second embodiment.

FIG. 7 is a diagram that schematically shows the configuration of a balloon catheter 10 in a second embodiment. FIG. 7 shows a configuration of a longitudinal section (YZ cross section) including a center axis AX of the balloon catheter 10. For convenience of illustration, regarding some configurations of the balloon catheter 10, a cross sectional configuration is not shown but a side surface configuration is shown, and some configurations of the balloon catheter 10 are not shown. In FIG. 7, Z axis positive direction side is the distal end side (distal side) to be inserted to a body, and Z axis negative direction side is the proximal end side (proximal side, near side) to be manipulated by a professional such as a doctor. FIG. 7 shows a state where the balloon catheter 10 is a straight line approximately parallel to the Z axis direction, as a whole, but the balloon catheter 10 is flexible enough to be bent. Note that herein regarding the balloon catheter 10 and each configuration member thereof, an end on the distal end side is referred to as "distal end", the distal end and a portion in the vicinity thereof are referred to as "distal end portion", an end on the proximal end side is referred to as "proximal end", and the proximal end and a portion in the vicinity thereof are referred to as "proximal end portion".

The balloon catheter 10 is a long medical device inserted to a body cavity such as a blood vessel for widening and expanding a lesion (constricted part or occluded part). The balloon catheter 10 of the present embodiment is a so-called rapid exchange type balloon catheter. The full length of the balloon catheter 10 is about 1500 mm, for example. The balloon catheter 10 is an example of the catheter in CLAIMS.

The balloon catheter 10 includes a balloon 20, an outer shaft 30, an inner shaft 50, a distal tip 80, and a connector 60 connected to a proximal end of the outer shaft 30.

The inner shaft 50 is a hollow long member formed with a lumen 51 to which a guide wire (not shown) is inserted, for example. The outer diameter of the inner shaft 50 ranges from about 0.2 mm to 2.0 mm, for example. Markers 25*a*, 25*b* having radiopacity are attached to a position in the inner shaft 50 in the inside of the balloon 20 so that the position of the balloon 20 can be grasped under irradiation. The number and position of the markers 25*a*, 25*b* may be appropriately changed depending on the length of the balloon 20. The inner shaft 50 is an example of the catheter shaft in CLAIMS.

The inner shaft 50 is made of a resin material. It is preferable that a resin material having a flexible property and appropriate flexibility be used as the resin material for forming the inner shaft 50. Examples of such a resin material include a polytetrafluoroethylene (PTFE) and a polyamide elastomer.

The distal tip 80 is a hollow member connected to the distal end portion of the inner shaft 50. The distal tip 80 is formed with a lumen 81 forming an integrated lumen by communicating with the lumen 51 of the inner shaft 50.

The distal tip 80 is made of a resin material. As the resin material for forming the distal tip 80, a resin material having higher flexibility (in other words, having lower hardness) than that of the resin material forming the inner shaft 50 is used. As the resin material for forming the distal tip 80, a resin material having lower melt viscosity than that of the resin material forming the inner shaft 50 is used. Examples of such a resin material include a polyurethane elastomer in a case where the inner shaft 50 is made of polytetrafluoroethylene or a polyamide elastomer.

The outer shaft 30 is a hollow member. The outer shaft 30 includes a distal end outer shaft portion 32, a guide wire port portion 33, an intermediate outer shaft portion 35, and a proximal end outer shaft portion 37 in this order from the distal end side. The distal end outer shaft portion 32 and the intermediate outer shaft portion 35 are cylindrical portions made of a resin material. The inner shaft 50 is inserted into the distal end outer shaft portion 32, and a lumen 31 for supplying fluid (contrast medium, physiological saline, or the like) for expanding the balloon 20 is formed between the distal end outer shaft portion 32 and the inner shaft 50. The guide wire port portion 33 is a portion where the distal end outer shaft portion 32, the intermediate outer shaft portion 35, and the inner shaft 50 are welded. The proximal end outer shaft portion 37 is a metallic tubular member referred to as a so-called hypotube. The distal end of the proximal end outer shaft portion 37 is inserted and welded to the proximal end of the intermediate outer shaft portion 35.

The balloon 20 is a member capable of expanding and contracting according to supply and discharge of fluid and is made of a resin material, for example. A distal end side fixation portion 22 of the balloon 20 is connected to the proximal end portion of the distal tip 80 and the distal end portion of the inner shaft 50 by welding, for example. A proximal end side fixation portion 23 of the balloon 20 is connected to the distal end portion of the outer shaft 30 by welding, for example.

Figure 8:
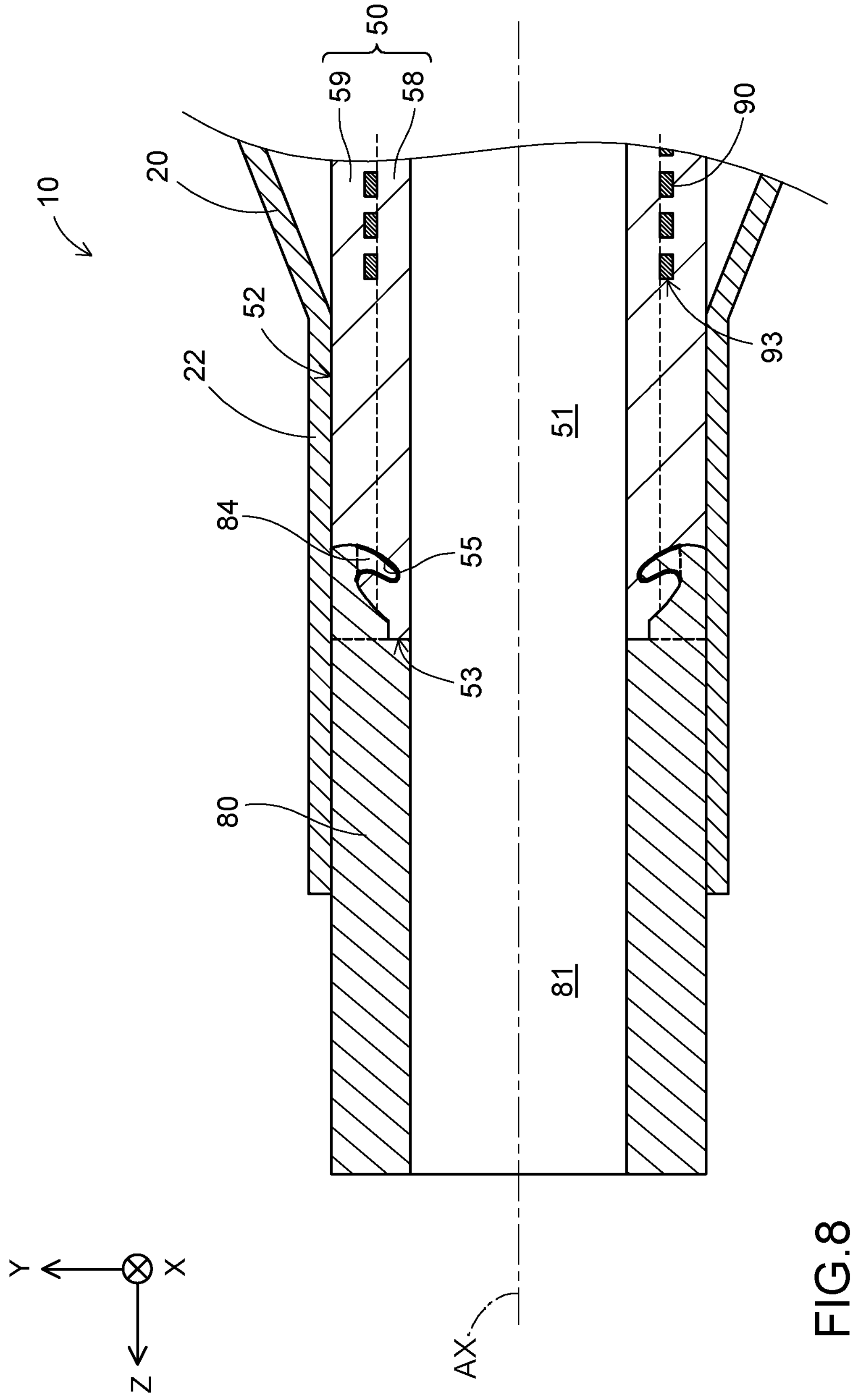
FIG. 8 is a diagram that shows a detailed configuration of a vicinity of a joint part of an inner shaft and a distal tip in the balloon catheter of the second embodiment.

FIG. 8 is a diagram that shows a detailed configuration of a vicinity of a joint part of the inner shaft 50 and the distal tip 80 in the balloon catheter 10 of the second embodiment. FIG. 8 shows the configuration of the longitudinal section (YZ cross section) of an X3 portion of FIG. 7 in an enlarged manner.

As shown in FIG. 8, the distal end portion of the inner shaft 50 is formed with a recess 55. Herein the recess 55 of the inner shaft 50 means a recess extending from the outer peripheral side of the balloon catheter 10 to the side close to the center axis AX, the recess being surrounded by the inner shaft 50 in a direction parallel to the center axis AX. As shown in FIG. 8, the recess 55 is located at the proximal end side from the distal end 53 of the inner shaft 50. In the present embodiment, the recess 55 opens in the outer peripheral surface 52 of the inner shaft 50.

The proximal end portion 84 of the distal tip 80 enters the recess 55 of the inner shaft 50. In the present embodiment, the proximal end portion 84 of the distal tip 80 is filled in the recess 55 with almost no gap.

In the present embodiment, in at least one longitudinal section (for example, the longitudinal section shown in FIG. 8) including the center axis AX of the balloon catheter 10, the proximal end portion 84 of the distal tip 80 (the portion of the distal tip 80 that enters the recess 55) extends in a diagonal direction from the proximal end side to the distal end side from the outer peripheral side of the balloon catheter 10 to the center axis AX side (in the example of FIG. 8, from upward to downward). As shown in FIG. 8, in the present embodiment, the extension direction of the proximal end portion 84 is a diagonal direction extending from the proximal end side to the distal end side over the entire height direction. A method of specifying the extension direction of the proximal end portion 84 in the section is similar to the method of specifying the extension direction of the proximal end portion 184 in the above-mentioned first embodiment. In the present embodiment, the configuration of the joint part of the distal tip 80 and the inner shaft 50 is similar over the entire circumference of the balloon catheter 10. That is, the balloon catheter 10 of the present embodiment has the configuration shown in FIG. 8 of the joint part of the distal tip 80 and the inner shaft 50 in any cross section including the center axis AX of the balloon catheter 10. A manufacturing method of the above-mentioned joint configuration of the inner shaft 50 and the distal tip 80 is similar to the manufacturing method of the joint configuration of the catheter shaft 150 and the distal tip 180 in the above-mentioned first embodiment.

As shown in FIG. 8, in the present embodiment, a reinforcing body 90 extending in the extension direction of the inner shaft 50 is arranged in the inside of the inner shaft 50. More specifically, the inner shaft 50 is a two-layer tube including a hollow inner layer 58 and an outer layer 59 covering the outer periphery of the inner layer 58. A coil made of metal, for example, is arranged as a reinforcing body 90 in between the inner layer 58 and the outer layer 59. The reinforcing body 90 is not arranged at the outermost distal end portion of the inner shaft 50. That is, the distal end 93 of the reinforcing body 90 is located at the proximal end side from the recess 55 of the inner shaft 50.

As described above, in the present embodiment, a resin material having higher flexibility than that of the resin material for forming the inner shaft 50 is used as the resin material for forming the distal tip 80, and specifically, a resin material having higher flexibility than that of the resin material for forming the outer layer 59 of the inner shaft 50 is used. The inner layer 58 and the outer layer 59 of the inner shaft 50 may be made of the same type of resin material or may be made of different types of resin material.

As described above, the balloon catheter 10 of the second embodiment includes the inner shaft 50 and the distal tip 80. The inner shaft 50 is a member including a distal end portion and a proximal end portion. The distal tip 80 is connected to the distal end portion of the inner shaft 50. The distal end portion of the inner shaft 50 is formed with the recess 55 at a position close to the proximal end side from the distal end 53 of the inner shaft 50. The distal tip 80 includes the proximal end portion 84 that enters the recess 55.

As described above, in the balloon catheter 10 of the second embodiment, since the proximal end portion 84 of the distal tip 80 enters the recess 55 formed in the inner shaft 50, a contact area of the distal tip 80 and the inner shaft 50 increases and the proximal end portion 84 of the distal tip 80 functions as an anchor. Therefore, according to the balloon catheter 10 of the second embodiment, the joint strength of the distal tip 80 and the inner shaft 50 can be sufficiently enhanced, and detachment of the distal tip 80 from the inner shaft 50 can be effectively prevented. The recess 55 may not be formed in the inner shaft 50 in advance, and such a configuration may be adopted that the recess 55 is formed when the proximal end portion 84 of the distal tip 80 enters the distal end portion of the inner shaft 50 as a result of jointing of the distal tip 80 to the inner shaft 50.

In the balloon catheter 10 of the second embodiment, at least a portion of the proximal end portion 84 of the distal tip 80 extends in a diagonal direction from the proximal end side to the distal end side from an outer peripheral side of the balloon catheter 10 to the center axis AX side of the balloon catheter 10, in a longitudinal sectional view of the balloon catheter 10. Therefore, according to the balloon catheter 10 of the second embodiment, since the proximal end portion 84 of the distal tip 80 further enters the inside of the inner shaft 50, the proximal end portion 84 can function as a more effective anchor. Therefore, according to the balloon catheter 10 of the present embodiment, the joint strength of the distal tip 80 and the inner shaft 50 can be more effectively enhanced, and detachment of the distal tip 80 from the inner shaft 50 can be more effectively prevented.

In the balloon catheter 10 of the second embodiment, the inner shaft 50 has an outer layer 59 made of a resin material, and the distal tip 80 is made of a resin material having lower hardness than hardness of the resin material for forming the outer layer 59 of the inner shaft 50. Therefore, according to the balloon catheter 10 of the second embodiment, since the distal tip 80 is made of the resin material having comparatively low hardness, flexibility of the distal end of the balloon catheter 10 can be secured, and a tissue in the body can be prevented from being damaged by the distal end of the balloon catheter 10. According to the balloon catheter 10 of the second embodiment, since the outer layer 59 of the inner shaft 50 is made of the resin material having comparatively high hardness, even when the heated formation material of the distal tip 80 is input into the recess 55 after the recess 55 is formed in the inner shaft 50, the shape of the distal end portion of the inner shaft 50 is maintained, and thereby, it is possible to easily and reliably achieve the configuration in which the proximal end portion 84 of the distal tip 80 enters the recess 55.

The balloon catheter 10 of the second embodiment further includes the reinforcing body 90 embedded in the inner shaft 50 and made of a coil. Therefore, since the inner shaft 50 is reinforced by the reinforcing body 90, the balloon catheter 10 can be provided with safety maintained. In the balloon catheter 10 of the second embodiment, the distal end 93 of the reinforcing body 90 is arranged at a position spaced from the recess 55 of the inner shaft 50 to the proximal end side. Therefore, the reinforcing body 90 can be prevented from being exposed from the inner shaft 50 even when heat or a mechanical force is applied, for example, at the time of forming the recess 55 in the inner shaft 50 or at the time of fixing the distal tip 80 to the inner shaft 50. Accordingly, according to the balloon catheter 10 of the second embodiment, the balloon catheter 10 can be provided with safety further maintained.

The balloon catheter 10 of the second embodiment further includes the balloon 20 including the distal end side fixation portion 22. The distal end side fixation portion 22 of the balloon 20 is connected to both the distal tip 80 and the inner shaft 50. Therefore, according to the balloon catheter 10 of the second embodiment, the joint strength of the distal tip 80 and the inner shaft 50 can be sufficiently enhanced by the presence of the proximal end portion 84 of the distal tip 80 functioning as an anchor. As a result, the distal end side fixation portion 22 of the balloon 20 can be prevented from being detached due to a malfunction of the joint part of the distal tip 80 and the inner shaft 50. According to the balloon catheter 10 of the second embodiment, the joint strength of the distal tip 80 and the inner shaft 50 can be further enhanced, and detachment of the distal tip 80 from the inner shaft 50 can be more effectively prevented.

In the balloon catheter 10 of the second embodiment, a portion of the distal end side fixation portion 22 of the balloon 20 is fixed to a position overlapping the proximal end portion 84 of the distal tip 80 in a radial direction of the balloon catheter 10. Therefore, according to the balloon catheter 10 of the second embodiment, the location provided with the proximal end portion 84 of the distal tip 80 can be reinforced by the presence of the distal end side fixation portion 22 of the balloon 20, the joint strength of the distal tip 80 and the inner shaft 50 can be more effectively enhanced, and detachment of the distal tip 80 from the inner shaft 50 can be more effectively prevented.

Figure 9:
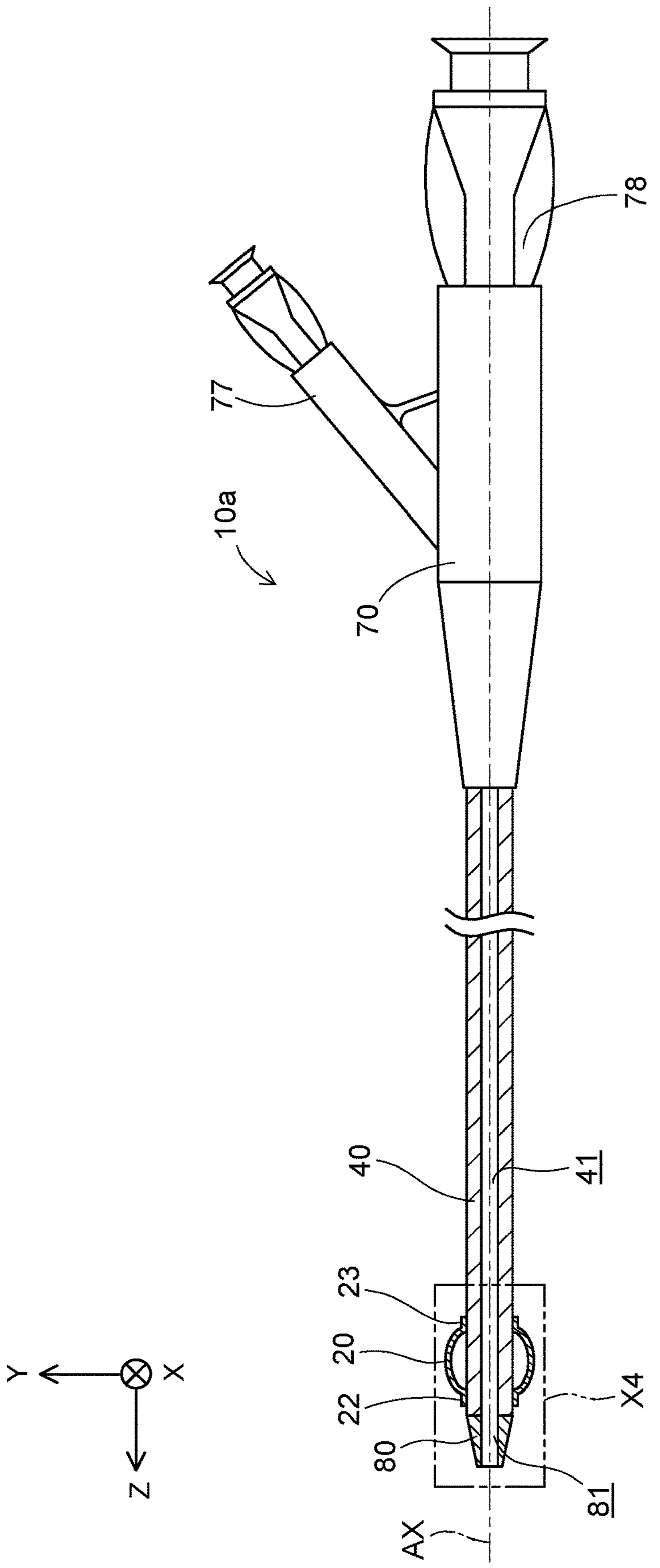
FIG. 9 is a diagram that shows a modification example of the second embodiment.
Figure 10:
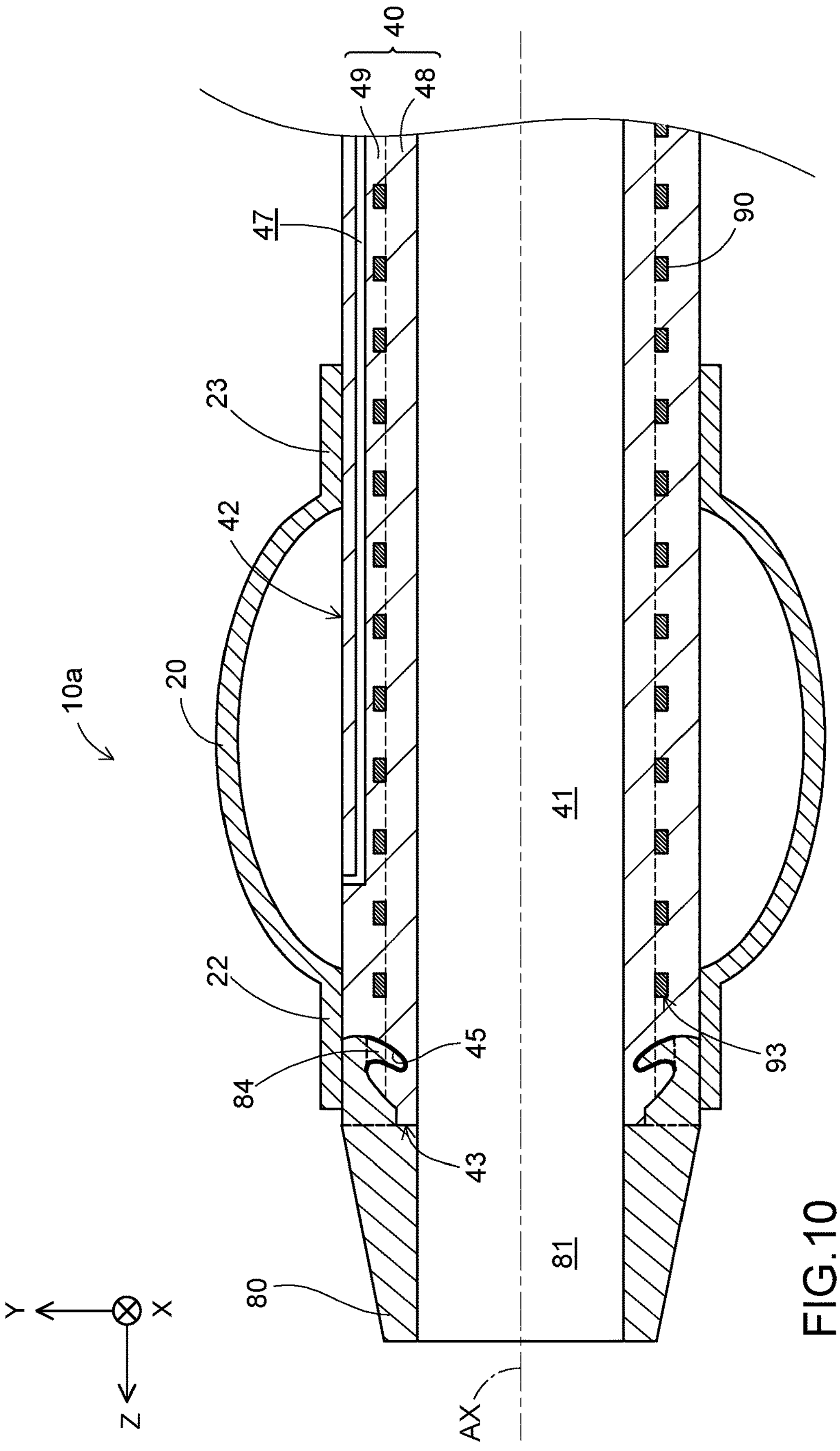
FIG. 10 is a diagram that shows a modification example of the second embodiment.

B-2. Modification Example of Second Embodiment:

In the above-mentioned second embodiment, a so-called rapid exchange type balloon catheter has been described as an example. However, the technology disclosed herein can be similarly applied to balloon catheter of other types. FIGS. 9 and 10 are diagrams that show a modification example of the second embodiment. The modification example of the second embodiment is an example in which the technology disclosed herein is applied to a so-called over-the-wire type balloon catheter. FIG. 9 shows the configuration of the longitudinal section (YZ cross section) including the center axis AX of the balloon catheter 10*a* in the modification example of the second embodiment, and FIG. 10 shows the configuration of the longitudinal section (YZ cross section) of an X4 portion of FIG. 9.

The balloon catheter 10*a* includes a balloon 20, a shaft 40, a distal tip 80, and a connector 70 connected to a proximal end of the shaft 40. The shaft 40 is an example of the catheter shaft in CLAIMS.

The distal tip 80 is connected to the distal end portion of the shaft 40. The distal tip 80 is formed with a lumen 81 forming an integrated lumen by communicating with the lumen 41 of the shaft 40. The integrated lumen communicates with an inner cavity of a treatment portion 78 formed in the connector 70. A distal end side fixation portion 22 of the balloon 20 is connected to the proximal end portion of the distal tip 80 and the distal end portion of the shaft 40 by welding, for example. A proximal end side fixation portion 23 of the balloon 20 is connected to the shaft 40 by welding, for example.

The shaft 40 is formed with a lumen 47 for supplying fluid for expanding the balloon 20. This lumen 47 communicates with an inner cavity of a fluid injection and discharge portion 77 formed in the connector 70.

As shown in FIG. 10, the distal end portion of the shaft 40 is formed with a recess 45. The recess 45 is located at the proximal end side from the distal end 43 of the shaft 40. The recess 45 opens in the outer peripheral surface of the shaft 40. The proximal end portion 84 of the distal tip 80 enters the recess 45 of the shaft 40.

A reinforcing body 90 is arranged in the inside of the shaft 40. That is, the shaft 40 is a two-layer tube including a hollow inner layer 48 and an outer layer 49 covering the outer periphery of the inner layer 48. A coil made of metal, for example, is arranged as the reinforcing body 90 in between the inner layer 48 and the outer layer 49. The distal end 93 of the reinforcing body 90 is located at the proximal end side from the recess 45 of the shaft 40. The distal end 93 of the reinforcing body 90 is located at a position overlapping the distal end side fixation portion 22 of the balloon 20 in a radial direction of the balloon catheter 10*a*.

According to the balloon catheter 10*a* of the modification example of the second embodiment shown in FIGS. 9 and 10, as similar to the balloon catheter 10*a* of the above-mentioned second embodiment, the distal tip 80 of the shaft 40 can be effectively prevented from being detached. That is, in the balloon catheter 10*a* of the modification example of the second embodiment, since the proximal end portion 84 of the distal tip 80 enters the recess 45 formed in the shaft 40, the contact area of the distal tip 80 and the shaft 40 increases, and the proximal end portion 84 functions as an anchor. Therefore, the joint strength of the distal tip 80 and the shaft 40 can be sufficiently enhanced and the distal tip 80 can be effectively prevented from being detached from the shaft 40.

In the balloon catheter 10*a* of the modification example of the second embodiment, the distal end 93 of the reinforcing body 90 is located at a position overlapping the distal end side fixation portion 22 of the balloon 20 in the radial direction of the balloon catheter 10*a*, the balloon 20 is reinforced by the reinforcing body 90 and it is possible to provide the balloon catheter 10*a* with safety maintained.

C. Modification Example

The technology disclosed herein is not limited to the above embodiments, and can be modified in various forms without departing from the gist thereof. For example, the following modification examples are also possible.

The configurations of the catheter 110 and the balloon catheter 10 in the embodiments described above and configurations of components included in those devices are merely examples and can be variously modified. For example, in the embodiments described above, the proximal end portion 184 (84) of the distal tip 180 (80) is filled in the recess 155 (55) with almost no gap. However, a little gap may be formed between the proximal end portion 184 (84) and the recess 155 (55).

Figure 11A:
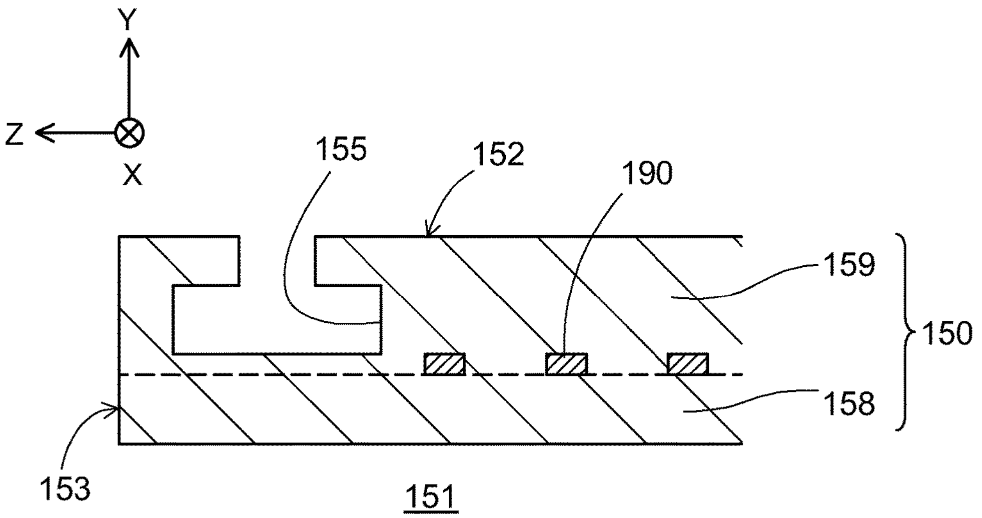
FIGS. 11A-11C are diagrams that show modification examples of a shape of a recess formed in a catheter shaft.
Figure 11B:
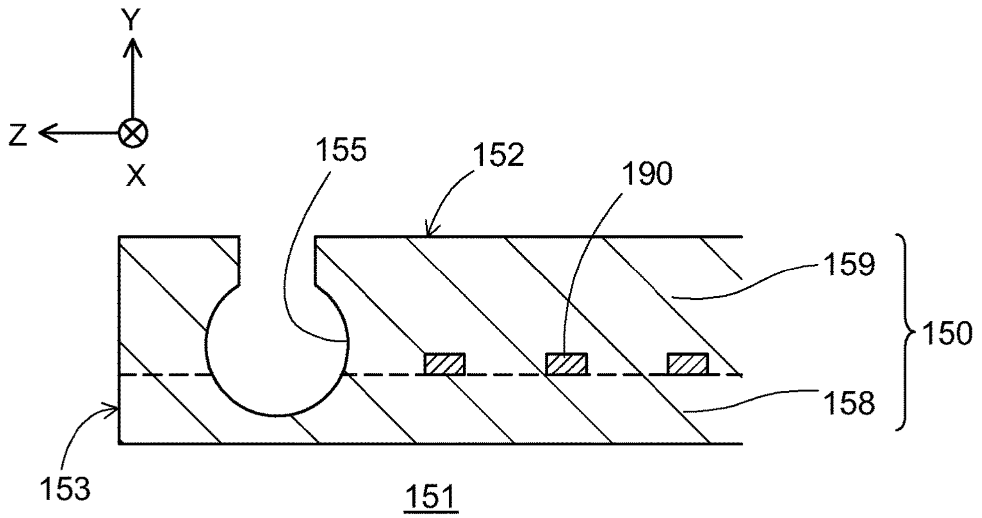
Figure 11C:
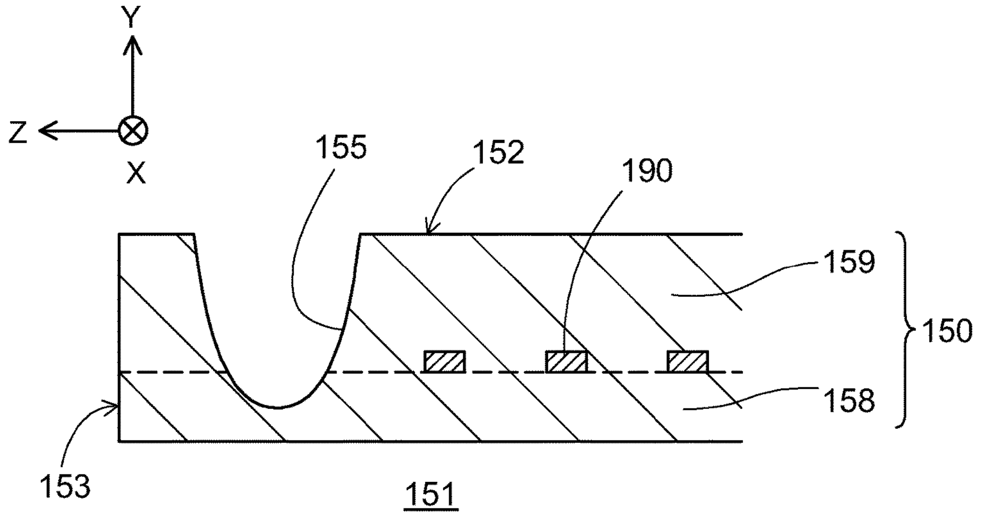
Figure 12A:
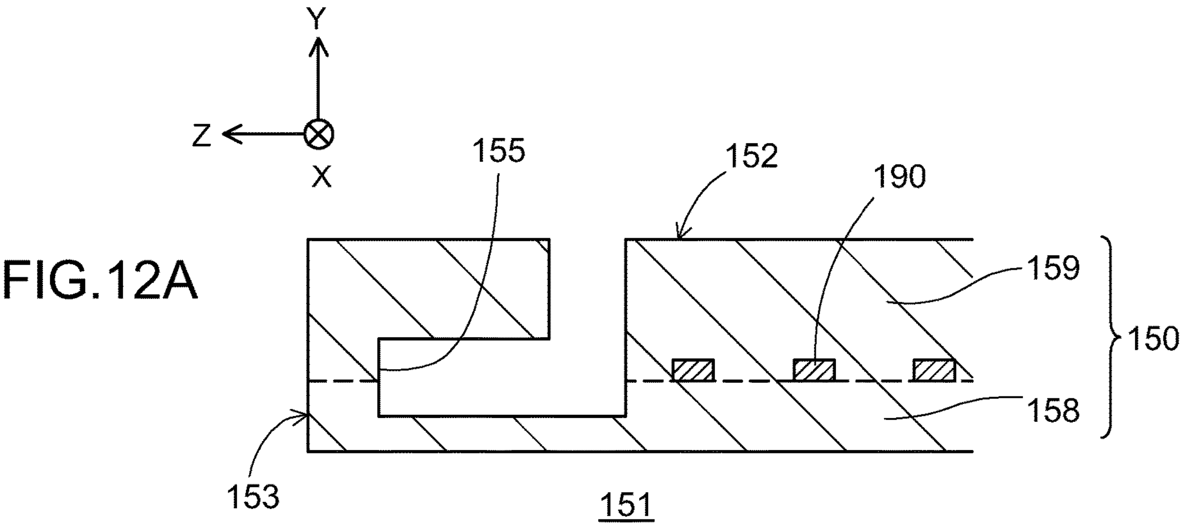
FIGS. 12A-12C are diagrams that show modification examples of a shape of the recess formed in the catheter shaft.
Figure 12B:
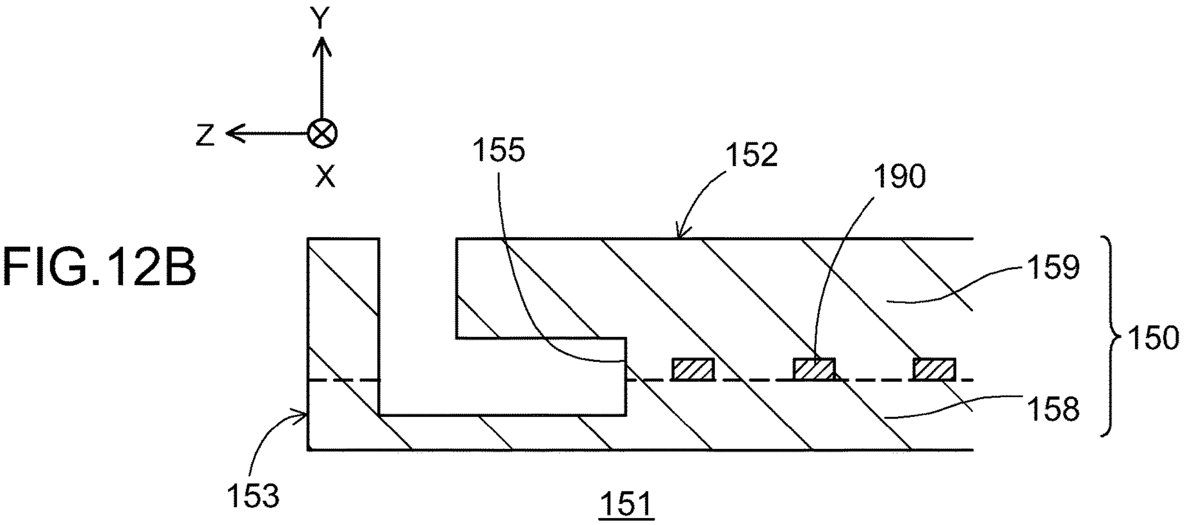
Figure 12C:
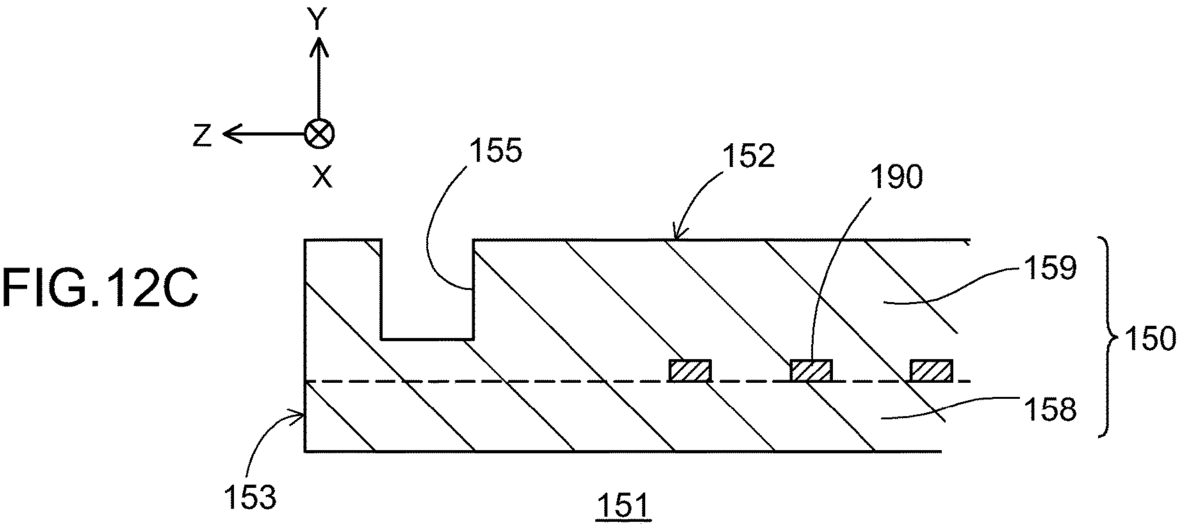
Figure 13A:
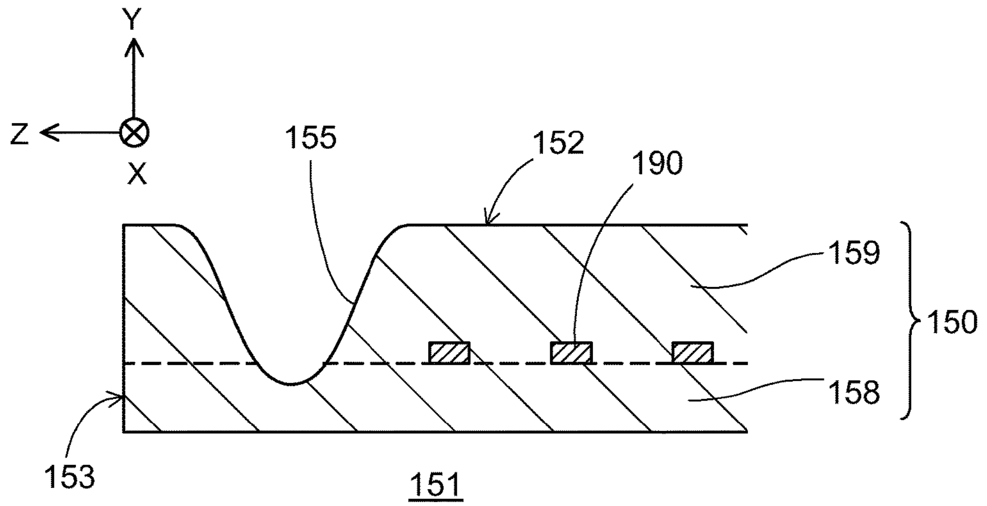
FIGS. 13A-13C are diagrams that show modification examples of a shape of the recess formed in the catheter shaft.
Figure 13B:
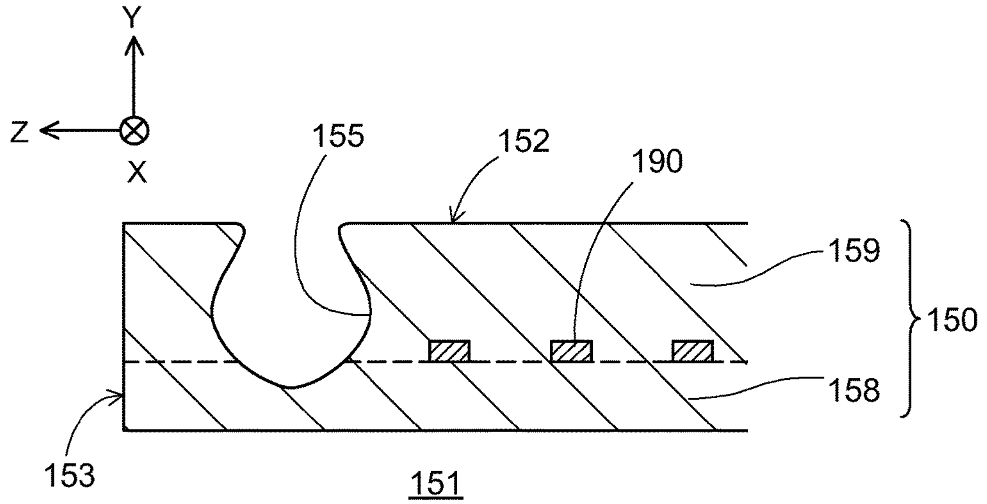
Figure 13C:
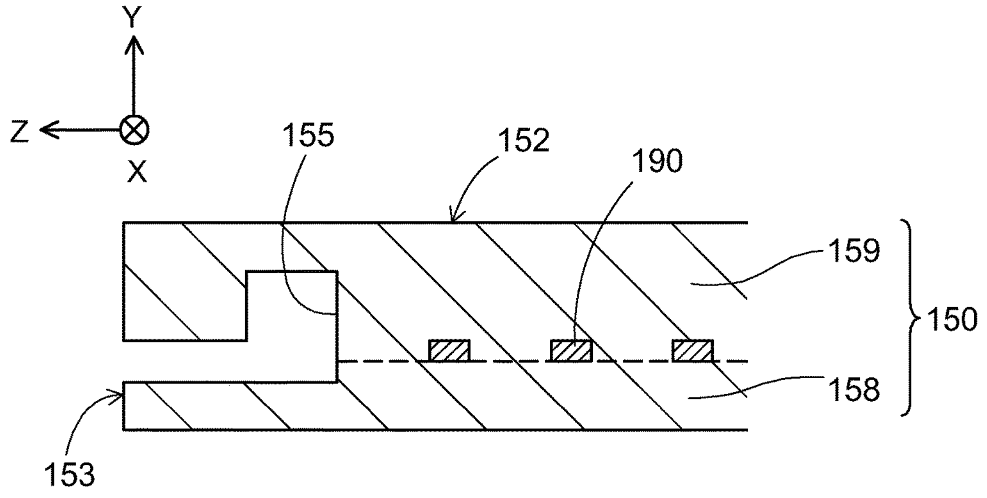

The shape of the recess 155 (or the recess 55, and so on) formed in the catheter shaft 150 (or inner shaft 50, and so on) in the embodiments described above is merely an example and can be variously modified. FIGS. 11A to 13C are diagrams that show a modification example of a shape of the recess 155 formed in the catheter shaft 150. FIGS. 11A to 13C show the configuration of the longitudinal section (YZ cross section) of the catheter shaft 150 including the center axis AX. As shown in FIG. 11A, the cross-sectional shape of the recess 155 may be a shape including a substantially rectangular portion, a thin-width portion extending from the vicinity of the center of the axial direction of the substantially rectangular portion to the outer peripheral surface 152 (more specifically, a portion excluding a portion forming an inner surface of the recess 155 in the outer peripheral surface 152, and so on). As shown in FIG. 11B, the cross-sectional shape may be a shape including a substantially circular portion and a thin-width portion extending from the vicinity of the center of the axial direction of the substantially circular portion to the outer peripheral surface 152. As shown in FIG. 11C, the cross-sectional shape may be a substantially bell shape in which the width increases as approaching the outer peripheral surface 152. As shown in FIG. 12A, the cross-sectional shape of the recess 155 may be a shape including a substantially rectangular portion, a thin-width portion extending from the vicinity of the proximal end portion of the substantially rectangular portion to the outer peripheral surface 152. As shown in FIG. 12B, the cross-sectional shape may be a shape including a substantially rectangular portion and a thin-width portion extending from the vicinity of the distal end portion of the substantially rectangular portion to the outer peripheral surface 152. As shown in FIG. 12C, the cross-sectional shape may be a substantially rectangular shape that opens in the outer peripheral surface 152. As shown in FIG. 13A, the cross-sectional shape of the recess 155 may be a substantially inverted-triangular shape in which the width increases as approaching the outer peripheral surface 152. As shown in FIG. 13B, the cross-sectional shape may be a substantially circular shape that opens in the outer peripheral surface 152. As shown in FIG. 13C, the cross-sectional shape may be a shape including a substantially rectangular portion, and a thin-width portion extending from the vicinity of the distal end portion of the substantially rectangular portion to a surface of the distal end 153 of the catheter shaft 150.

In the second embodiment described above, the reinforcing body 90 is arranged in the inside of the inner shaft 50. However, the reinforcing body 90 may be arranged along the inner shaft 50 in the outside of the inner shaft 50. As the reinforcing body 90, other material than the coil such as braiding may be used. In the second embodiment described above, the reinforcing body 90 may be omitted.

In the second embodiment described above, the inner shaft 50 has a two-layer configuration. However, the inner shaft 50 may have a single layer configuration or a configuration of three or more layers. In the second embodiment described above, the distal end side fixation portion 22 of the balloon 20 is connected to both the distal tip 80 and the inner shaft 50. However, the distal end side fixation portion 22 of the balloon 20 may be connected to one of the distal tip 80 and the inner shaft 50.

In the second embodiment described above, the configuration of the joint part between the distal tip 80 and the inner shaft 50 is similar over the entire circumference of the balloon catheter 10. However, it is sufficient that the configuration of the joint part is adopted in at least a portion of the entire circumference of the balloon catheter 10. In the second embodiment described above, a modification example similar to the modification example of the first embodiment shown in FIGS. 4A, 4B, and 5A, 5B.

In the first embodiment described above, the catheter shaft 150 has a single layer configuration. However, the catheter shaft 150 may have a multilayer configuration. When the catheter shaft 150 has a multilayer configuration, as the resin material for forming the distal tip 180, a resin material having higher flexibility than that of the resin material forming the outermost layer of the catheter shaft 150 is used. A reinforcing body such as a coil, braiding, or the like may be arranged in the inside of the catheter shaft 150.

In the first embodiment described above, the configuration of the joint part between the distal tip 180 and the catheter shaft 150 is similar over the entire circumference of the catheter 110. However, it is sufficient that the configuration of the joint part is adopted in at least a portion of the entire circumference of the catheter 110.

In the embodiment described above, in the distal end portion of the catheter shaft 150 (or the inner shaft 50, and so on), the recess 155 (or the recess 55, and so on) is formed at a position close to the proximal end side from the distal end 153 (or the distal end 53, and so on) of the catheter shaft 150. However, the recess 155 may be formed in the distal end 153 of the catheter shaft 150.

The formation materials for each member in each of the above embodiments are only examples, and can be changed variously. The manufacturing methods of the catheter 110 and the balloon catheter 10 in each of the embodiments described above are merely examples. The catheter 110 and the balloon catheter 10 may be manufactured by other method.

REFERENCE SIGNS LIST

10: Balloon catheter, 20: Balloon, 22: Distal end side fixation portion, 23: Proximal end side fixation portion, 25*a*, 25*b*: Marker, 30: Outer shaft, 31: Lumen, 32: Distal end outer shaft portion, 33: Guide wire port portion, 35: Intermediate outer shaft portion, 37: Proximal end outer shaft portion, 40: Shaft, 41: Lumen, 43: Distal end, 45: Recess, 47: Lumen, 48: Inner layer, 49: Outer layer, 50: Inner shaft, 51: Lumen, 52 Outer peripheral surface, 53: Distal end, 55: Recess, 58: Inner layer, 59: Outer layer, 60: Connector, 70: Connector, 77: Fluid injection discharge portion, 78: Treatment portion, 80: Distal tip, 81: Lumen, 84: Proximal end portion, 90: Reinforcing body, 93: Distal end, 110: Catheter, 150: Catheter shaft, 151: Lumen, 152: Outer peripheral surface, 153: Distal end, 155: Recess, 156: Deficit portion, 158: Inner layer, 159: Outer layer, 160: Connector, 180 Distal tip, 181: Lumen, 184: Proximal end portion, 190: Reinforcing body, 193: Distal end

The invention claimed is:

1. A catheter comprising:

a catheter shaft including a distal end portion and a proximal end portion; and a distal tip connected to the distal end portion of the catheter shaft, wherein:

a single recess is formed in the distal end portion of the catheter shaft, and the distal tip includes a proximal end portion that is inserted into the recess.

2. The catheter according to claim 1, further comprising a reinforcing body embedded in the catheter shaft and formed of a coil or braiding.

3. The catheter according to claim 2, wherein a distal end of the reinforcing body is spaced from the recess in a proximal direction towards a proximal end side of the catheter shaft.

4. The catheter according to claim 1, wherein at least a portion of the proximal end portion of the distal tip extends in a direction that is:

substantially orthogonal to a center axis of the catheter so that at least the portion of the proximal end portion extends inwardly from an outer peripheral side of the catheter towards the center axis, or inclined with respect to the center axis of the catheter so that at least the portion of the proximal end portion extends inwardly from the outer peripheral side towards the center axis and is inclined in a direction extending from a proximal end side towards a distal end side of the catheter.

5. The catheter according to claim 1, wherein the distal tip is made of a resin material having a lower hardness than a hardness of a resin material forming the catheter shaft.

6. The catheter according to claim 1, wherein the distal tip is made of a resin material having a lower melt viscosity than a melt viscosity of the resin material forming the catheter shaft.

7. The catheter according to claim 1, wherein the recess opens in a distal end of the catheter shaft.

8. The catheter according to claim 1, further comprising a balloon including a distal end side fixation portion that is connected to at least one of the distal tip and the catheter shaft.

9. The catheter according to claim 8, further comprising a reinforcing body embedded in the catheter shaft and made of a coil or braiding, wherein a distal end of the reinforcing body is located at a position overlapping the distal end side fixation portion of the balloon in a radial direction of the catheter.

10. The catheter according to claim 8, wherein a portion of the distal end side fixation portion of the balloon is fixed to at least one of the distal tip and the catheter shaft at a position overlapping the proximal end portion of the distal tip in a radial direction of the catheter.

11. The catheter according to claim 1, wherein no part of the catheter shaft is located on an outer circumference of the distal tip.

12. The catheter according to claim 1, wherein a maximum outer diameter of the distal tip is the same as a maximum outer diameter of the distal end portion of the catheter shaft.

13. The catheter according to claim 1, wherein at least a portion of the proximal end portion of the distal tip extends in a direction that is inclined with respect to a center axis of the catheter so that at least the portion of the proximal end portion extends inwardly from an outer peripheral side towards the center axis and is inclined in a direction extending from a proximal end side towards a distal end side of the catheter.

14. The catheter according to claim 13, wherein the recess opens onto an outer surface of the catheter shaft.

* * * * *